United States Patent
Hirsch et al.

(10) Patent No.: US 10,828,486 B2
(45) Date of Patent: Nov. 10, 2020

(54) METHOD FOR MANUFACTURING ELECTRICAL CONDUCTORS, AND ELECTRICAL CONDUCTORS MANUFACTURED ACCORDING TO SAME

(71) Applicant: ECOLE POLYTECHNIQUE FEDERALE DE LAUSANNE (EPFL), Lausanne (CH)

(72) Inventors: Arthur Hirsch, Lausanne (CH); Hadrien Michaud, Lausanne (CH); Ivan Rusev Minev, Lausanne (CH); Stephanie P. Lacour, Daillens (CH)

(73) Assignee: ECOLE POLYTECHNIQUE FEDERALE DE LAUSANNE (EPFL), Lausanne (CH)

( * ) Notice: Subject to any disclaimer, the term of this patent is extended or adjusted under 35 U.S.C. 154(b) by 0 days.

(21) Appl. No.: 15/765,987

(22) PCT Filed: Oct. 28, 2016

(86) PCT No.: PCT/EP2016/076174
§ 371 (c)(1),
(2) Date: Apr. 4, 2018

(87) PCT Pub. No.: WO2017/072347
PCT Pub. Date: May 4, 2017

(65) Prior Publication Data
US 2018/0289946 A1 Oct. 11, 2018

(30) Foreign Application Priority Data

Oct. 30, 2015 (EP) .................................... 15192402

(51) Int. Cl.
*C22C 1/00* (2006.01)
*A61N 1/04* (2006.01)
(Continued)

(52) U.S. Cl.
CPC .......... *A61N 1/0496* (2013.01); *A61B 5/0408* (2013.01); *A61N 1/0456* (2013.01);
(Continued)

(58) Field of Classification Search
None
See application file for complete search history.

(56) References Cited

U.S. PATENT DOCUMENTS

2018/0168033 A1* 6/2018 Letizia ................ H05K 1/0283

FOREIGN PATENT DOCUMENTS

| JP | H11-220182 A | 8/1999 |
| WO | 2015/073944 A2 | 5/2015 |

OTHER PUBLICATIONS

Michaud et al. "Soft metal constructs for large strain sensor membrane" (Feb. 2015) Smart Materials and Structures, vol. 24, No. 3 (Year: 2015).*

(Continued)

*Primary Examiner* — Jose I Hernandez-Kenney
(74) *Attorney, Agent, or Firm* — Seed Intellectual Property Law Group LLP

(57) ABSTRACT

A method for manufacturing an electrical conductor includes: depositing a solid metal conductive layer or film on a substrate 30; depositing a liquid metal on the solid layer; and allowing the liquid metal and the solid layer 40 to alloy by diffusion of the liquid metal into the solid layer or film so as to form a solid conductive layer or film of the alloy; as well as allowing the liquid metal to further infiltrate the alloy so as to form percolating paths and/or droplets of the liquid metal in the the solid conductive layer or film, thus forming a biphasic conductive layer.

11 Claims, 6 Drawing Sheets

Alloyed layer and liquid gallium accumulation after gallium evaporation on alloying layer

(51) Int. Cl.
*C22C 28/00* (2006.01)
*C22C 5/02* (2006.01)
*H05K 1/02* (2006.01)
*A61N 1/05* (2006.01)
*A61B 5/0408* (2006.01)
*H01B 1/02* (2006.01)
*H05K 1/09* (2006.01)
*A61B 5/0478* (2006.01)

(52) U.S. Cl.
CPC ............... *A61N 1/05* (2013.01); *C22C 1/005* (2013.01); *C22C 5/02* (2013.01); *C22C 28/00* (2013.01); *H01B 1/02* (2013.01); *H05K 1/0283* (2013.01); *H05K 1/09* (2013.01); *A61B 5/0478* (2013.01); *A61B 2562/125* (2013.01); *A61B 2562/166* (2013.01); *H05K 2201/0391* (2013.01); *H05K 2203/128* (2013.01)

(56) References Cited

OTHER PUBLICATIONS

Kim et al., "A Biaxial Stretchable Interconnect With Liquid-Alloy-Covered Joints on Elastomeric Substrate," *Journal of Microelectromechanical Systems* 18(1):138-146, 2009.

Kim et al., "Interfacing Liquid Metals with Stretchable Metal Conductors," *Applied Materials & Interfaces* 7(15):7920-7926, 2015.

Michaud et al., "Soft Flexion Sensors Integrating Strechable Metal Conductors on a Silicone Substrate for Smart Glove Applications," *28th IEEE International Conference on Micro Electro Mechanical Systems*, Estoril, Portugal, Jan. 18-22, 2015, pp. 760-763.

Michaud et al., "Soft metal constructs for large strain sensor membrane," *Smart Materials and Structures* 24(3):035020, 2015. (9 pages).

\* cited by examiner

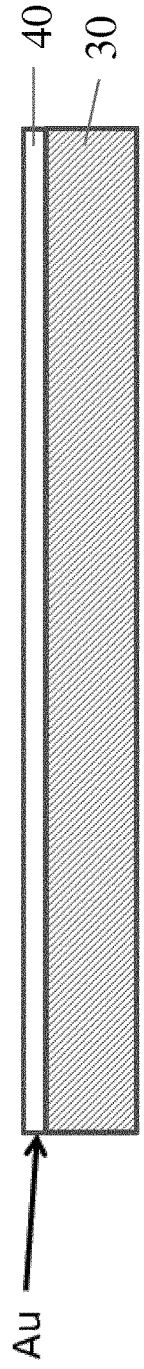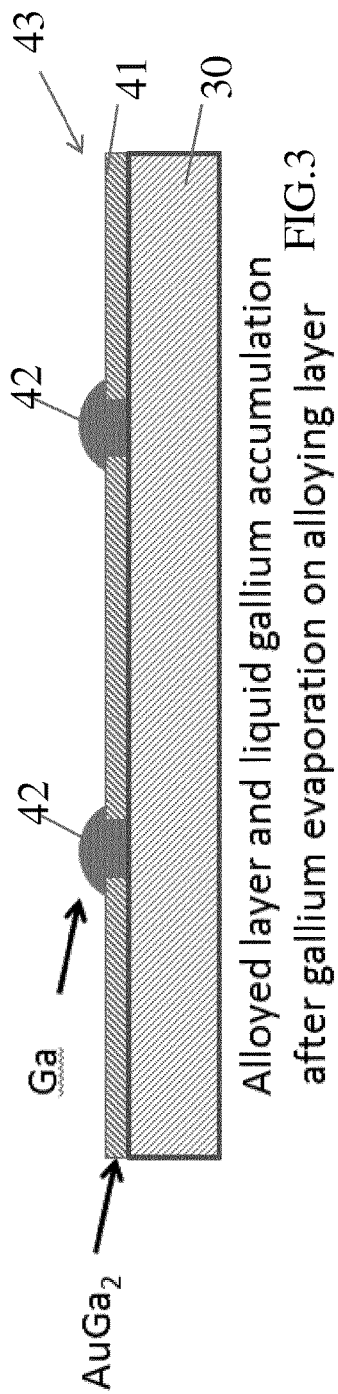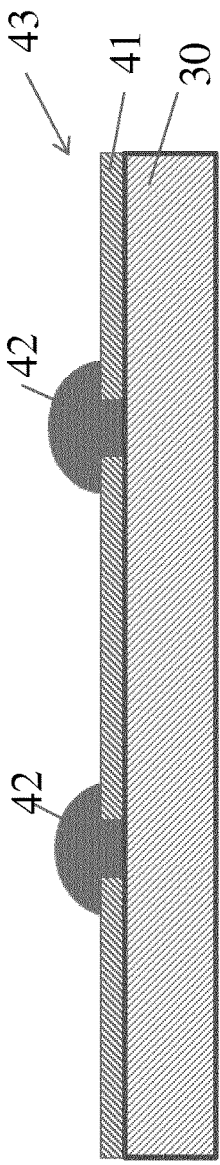

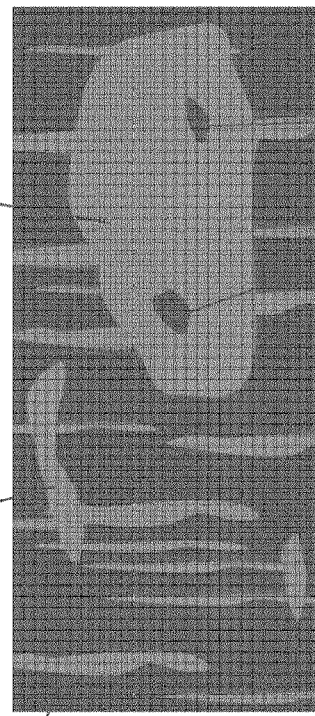
FIG. 6 Under strain
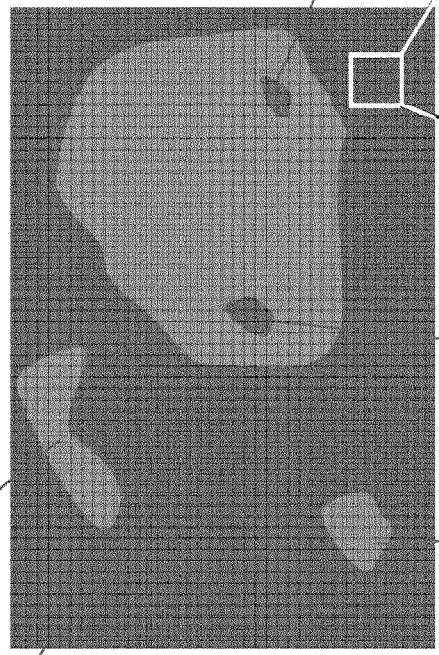
FIG. 5 At rest
top view
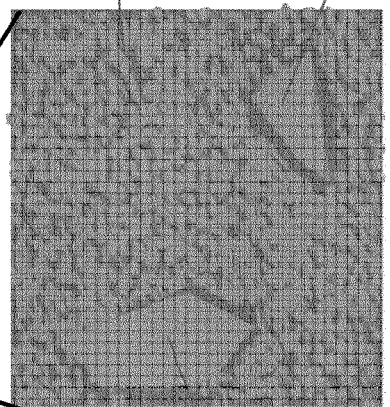
FIG. 5a
AuGa$_2$/Ga
Ga
AuGa$_2$
  

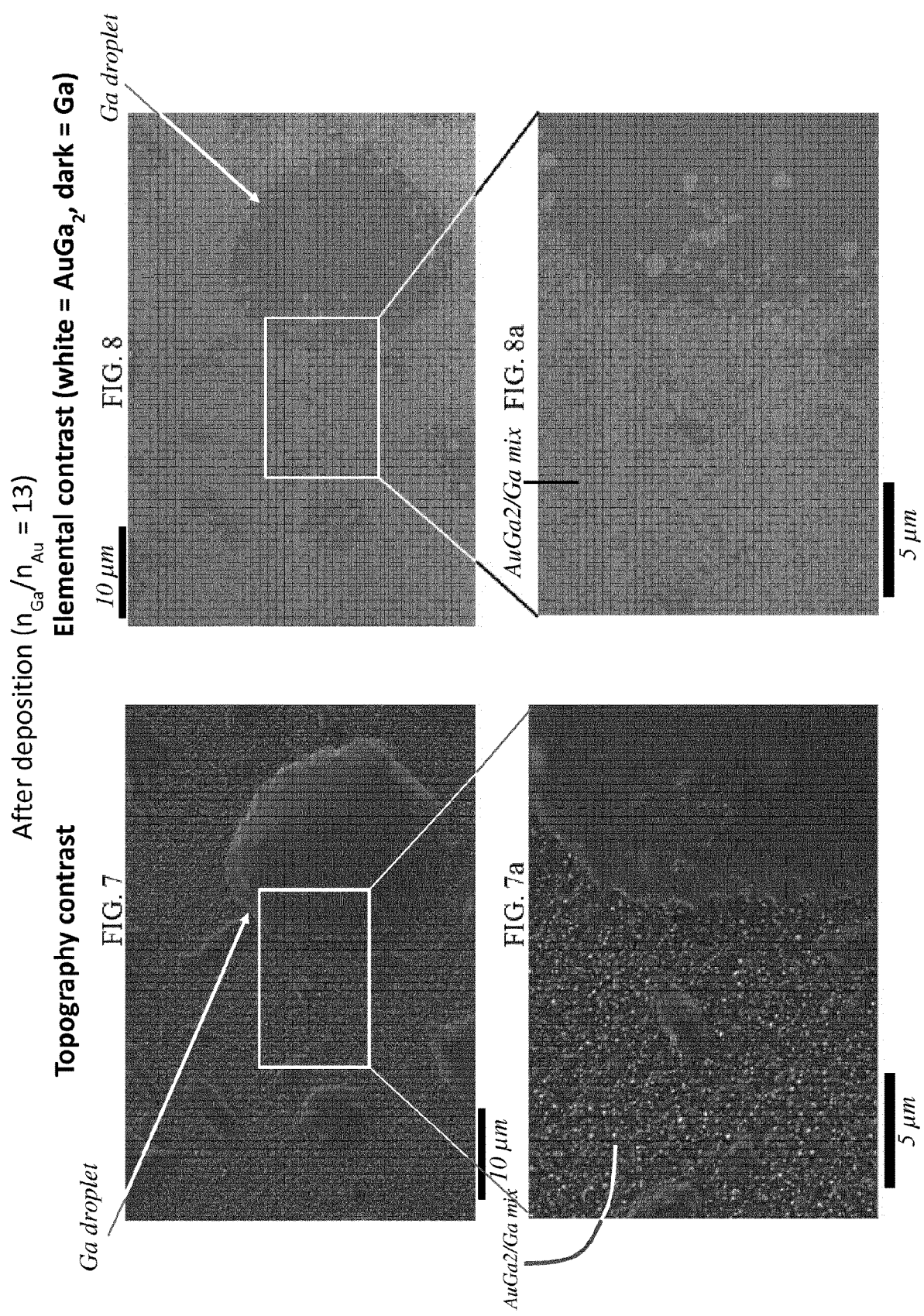

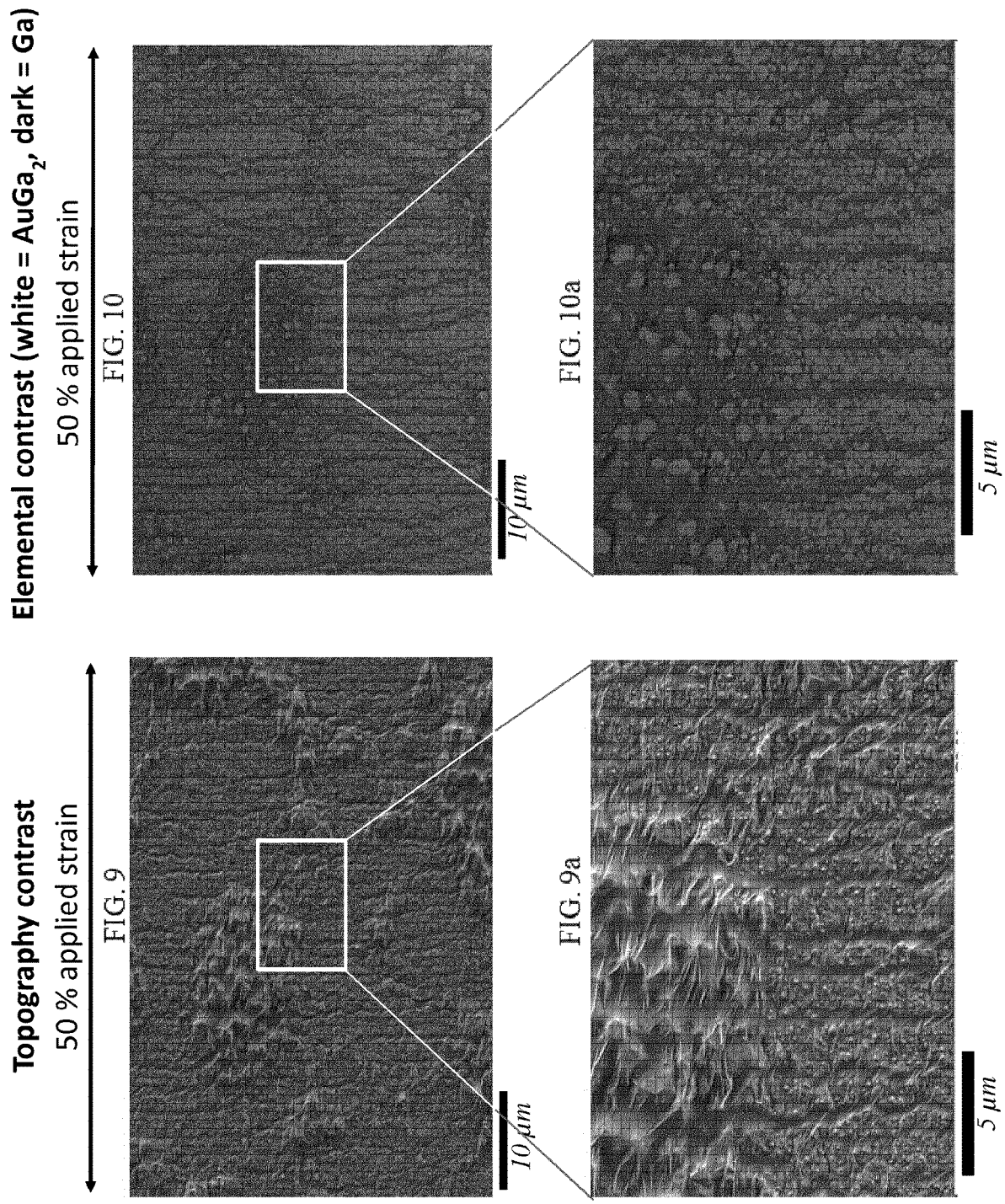

METHOD FOR MANUFACTURING ELECTRICAL CONDUCTORS, AND ELECTRICAL CONDUCTORS MANUFACTURED ACCORDING TO SAME

BACKGROUND

Technical Field

The present invention belongs to the field of electrical conductors, electrical conductive strips, paths, lines, arrays or the like. In particular, the present invention relates to elastic, preferably highly conductive electrical connectors such as bendable and/or stretchable electrical conductors. In more detail, the present invention relates to a method for manufacturing electrical conductors, electrical conductive strips, paths, lines, arrays or the like. According to the present invention there is further provided a method for manufacturing electrodes or conductive paths in general, in particular for manufacturing stretchable electrical conductors, electrode arrays, paths, strips or the like. Still in more details, according to the present invention liquid and solid metals are used, in combination, for producing and/or manufacturing electrical conductors, electrode arrays, conductive circuits, paths, strips or the like, in particular bendable and/or stretchable.

Description of the Related Art

Flexible and/or bendable and/or stretchable conductors such as, for instance, conductive arrays, paths, strips, lines or the like are becoming more and more popular and find use in several applications. For instance, stretchable arrays comprising thin or even ultrathin conductive films (made of either metal or conductive elastomer composites) are becoming more and more popular and find convenient applications in the fields of, for instance, wearable electronics, and/or soft robotics and/or implantable neuroprosthetic interface applications, and/or as electrode arrays for in vitro cell culture and tissue slice culture or the like; in fact, the most important characteristic or feature of stretchable microelectrode arrays, films, strips or lines of the kind mentioned above, relates to the fact that same can withstand mechanical deformations such as flexion, stretch, torsion or the like, without electrical failure or loss of their electrical features and properties (in particular of their electrical conductivity).

Accordingly, stretchable conductive micro arrays or circuits, films, paths or the like (in the following referred to as stretchable (conductive) interconnections) are particularly suitable to be used as a bioelectronics interface with the spinal cord, brain or peripheral nerves or soft biological tissue, for instance for the purpose of stimulating and/or recording neurological or cardiac activity (both in vitro and in vivo), as well as for monitoring hippocampal electrical activity after traumatic brain injury or bladder afferent activity, or even for stimulating electrical potential of excitable cells or the like.

Among other usual and very convenient applications of stretchable conductive micro arrays, films, paths, lines or the like, their use as, for instance, stretchable conductors for stretchable PCBs (Printed Circuit Boards), and/or stretchable interconnections, and/or sensing materials or the like may be mentioned.

It has in fact been verified that the electrical properties of stretchable interconnections are maintained during their deformation and even after repeated torsions, extensions, and therefore facilitate both the recording and the transmission of small amplitude signals (for instance biological) and ensure therefore the required reliability in each of the above mentioned applications. In particular, in both cases of in vitro and in vivo applications, stretchable interconnections did not show any degradation of the implant electrical functionality, even after several months from implantation.

In the most common stretchable interconnections according to the prior art, the conductive strips or films may be formed by using either solid or liquid conductive materials. In particular, as to the prior art interconnections with solid conductive films, same may be formed according to one of the following solutions:

a) inducing conductivity in inherently non-conductive elastic materials (for instance by adding carbon to an elastomer);

b) engineering elasticity within a non-elastic but conductive film (for instance by forming microcracks in a gold film);

c) engineering elasticity in a non-elastic but conductive film (for instance by macroscopic patterning the film to enable buckling).

Several disadvantages and/or drawbacks are however still related to stretchable interconnections (both stretchable and non-stretchable) with solid conductive films formed according to one of the above mentioned solutions a) to c), such as, for instance, low electrical conductivity a (ranging from 100 to 1000 S/cm in the case of films of composite materials according to solution a), amounting to $10^6$ S/cm for microcracked Au according to solution b)).

The above disadvantages and/or drawbacks strongly limit the convenient applications of interconnections with solid tracks or films.

Moreover, as a further drawback, the density of the solid conductive tracks is strongly limited by the need of carrying out very complex, multistep processes (comprising transient packaging), which moreover result in very high manufacturing and/or production costs.

In an attempt to overcome the above summarized drawbacks, stretchable interconnections with liquid conductive strips, films, paths or the like (obtained for instance by deposing a liquid film on an elastic substrate and subsequently patterning the film) have been proposed in the recent years. However, a deep investigation as to the real advantages offered by liquid metals is still needed. Furthermore, reliable and cost efficient manufacturing processes for the batch production of stretchable interconnections using liquid metals are still mostly not available to the manufacturers.

For instance, in those cases in which the conductive films are formed by injecting a liquid metal, micro channels have to be formed on a substrate for hosting the liquid metal; however, in these cases manufacturing costs arise and the density of the conductive strips is strongly limited by the micro channels.

As to conductive films formed by printing a liquid metal on a substrate, the films may not be formed as thin as required by the most common integrated microelectronics circuits (see above).

It is therefore an object of the present invention that of overcoming or at least reducing the drawbacks affecting both the stretchable interconnections and methods for manufacturing same according to the prior art.

In particular, a goal of the present invention is that of proposing a solution allowing to overcome the drawbacks affecting the interconnections according to the prior art, in particular both those comprising solid conductive strips or tracks and those comprising liquid conductive strips or tracks.

In detail, a further goal of the present invention is that of proposing a method for the reliable and easy formation of very thin (<5 µm) conductive interconnections (both stretchable and non-stretchable, depending on the needs and/or circumstances) with films, paths, arrays or the like with high or even very high (and stable) electrical conductivity.

Moreover, according to the present invention, stretchable interconnections shall be manufactured with a limited need of carrying out complex, multistep processing and at low or at least contained costs, wherein it shall be possible to pattern the conductive films with very high in-plane aspect ratios and limited or contained thickness.

BRIEF SUMMARY

The methods according to the present invention have revealed to be particularly suitable and/or convenient for manufacturing conductive stretchable circuits, arrays and/or interconnections in general.

Accordingly, this is the reason why, in the following, description will be given of examples according to which the methods according to the present invention are carried out for manufacturing stretchable circuits and/or interconnections.

However, it has to be noted that the possible applications of the methods according to the present invention are not limited to the manufacturing of stretchable circuits and/or interconnections; to the contrary, the methods according to the present invention are adapted to be carried out for the formation on any substrate of either stretchable or not stretchable circuits, arrays, paths, films or the like and conductors in general.

The present invention is based on the consideration that the drawbacks affecting the methods according to the prior art for 30 manufacturing conductive interconnections, in particular stretchable, may be efficiently and conveniently overcome by using, for the formation of conductive strips on a substrate, both solid and liquid metals.

A further consideration on which the present invention is based relates to the fact that by opportunely selecting both the solid and the liquid metals, and by bringing them into contact, a conductive film or strip can be formed comprising both a solid alloy and residual liquid metal, thus offering excellent stretchability and conductivity.

A further consideration on which the present invention is based relates to the fact that liquid metals (such as gallium or eutectic gallium indium (EGaIn)) typically do not wet stretchable substrates (such as silicone). By depositing a well-selected metal layer on the substrate prior to liquid metal deposition, the liquid metal alloys with the metal layer in a first stage and enhances the wettability. Then, an excess of liquid metal is further deposited to enhance conductivity and stretchability of the resulting film. The selected deposition method for the liquid metal (as an example, physical vapor deposition) enables control of the ratio n between the number of atoms of liquid metal and the number of atoms of solid metal in the resulting biphasic (solid-liquid) layer or film, in order to maintain a micrometric thickness while guaranteeing high conductivity and high stretchability of the obtained films.

Still according to the considerations on the basis of the present invention further advantages arise by opportunely selecting the methods and/or processes for bringing into contact the solid and liquid metals used for forming the conductive strips, films, paths and interconnections in general.

On the basis of the considerations as stated above, a first embodiment of the present invention relates to a method for manufacturing an electrical conductor, said method comprising:

providing a substrate;
depositing a solid metal conductive layer or film on said substrate;
depositing a liquid metal on said solid layer;
allowing said liquid metal and said solid layer to alloy by diffusion of said liquid metal into said solid layer or film so as to form a solid conductive layer or film of said alloy;
allowing said liquid metal to further infiltrate said alloy so as to form percolating paths of said liquid metal in said solid conductive layer or film, thus forming a biphasic conductive layer comprising said solid alloy as a solid phase and said paths of said liquid metal as a liquid phase dispersed therein.

According to an embodiment, said method may further comprise allowing said liquid metal to further accumulate into bulges, locally yet randomly, on or within said biphasic conductive layer.

According to an embodiment, said liquid metal may be deposited on said solid conductive metal layer or film by thermal vapour deposition of said liquid metal.

According to a further embodiment said liquid metal may comprise one of gallium and a gallium-based alloy.

According to a further embodiment, said solid metal conductive layer or film may be sputtered on said substrate.

Eventually, said solid layer may be made of one of Au, Pd, Pt, Ir, and an alloy thereof.

Preferably, the thickness of said solid layer is between 10 and 1000 nm, more preferably 60 nm Advantageously, the ratio n between the number of atoms of said liquid metal and the number of atoms of said solid metal in said biphasic layer or film is between 2 and 50, preferably 13.

According to an embodiment, said substrate may be an elastomeric substrate, preferably a silicone or a polydimethylsiloxane (PDMS) substrate.

Further embodiments of the method according to the present invention are specified in the appended method claims.

The present invention further relates to an electrical conductor manufactured by carrying out one of the methods according to the present invention, for instance one of them as summarized above, said electrical conductor comprising:

a substrate and a conductive layer or film on said substrate;
wherein said conductive layer or film is a biphasic conductive layer with a solid metal alloy as a solid phase and percolating paths and bulges of a liquid metal as a liquid phase dispersed therein.

According to an embodiment, said solid metal alloy may be an alloy of one of gallium and a gallium-based alloy, alloyed with one of Au, Pd, Pt, Ir and an alloy thereof.

According to a further embodiment, said percolating paths and bulges of a liquid metal are made of one of gallium and a gallium-based alloy.

According to a further embodiment, the thickness of said solid metal alloy layer or film may be between 10 and 1000 nm, preferably 60 nm Eventually, the ratio n between the number of atoms of said liquid metal and the number of atoms of said solid metal in said biphasic layer or film may be between 2 and 50, preferably 13.

According to the needs and/or circumstances, said substrate may be an elastomeric substrate, preferably a silicone or a PDMS substrate.

Further eventual embodiments of one or both of the method and conductor according to the present invention are defined in the appended claims.

BRIEF DESCRIPTION OF THE DRAWINGS

In the following, description will be given of the embodiments of the present invention depicted in the drawings. It has however to be noted that the present invention is not limited to the embodiments depicted in the drawings and described below; to the contrary, the present invention comprises all those embodiments which fall within the scope of the appended claims.

In the drawings:

FIGS. 1, 2, 3 and 4 depict method steps of a method according to a first embodiment of the present invention;

FIGS. 5, 5a and 6 show schematic representations or views of a conductive film according to one embodiment of the present invention;

FIGS. 7, 7a and 8, 8a show scanning electron microscope (SEM) images of a conductive film according to an embodiment of the present invention;

FIGS. 9, 9a and 10, 10a show SEM images of the conductive film depicted in FIGS. 7, 7a and 8, 8a, respectively, when subjected to a strain or stretch.

DETAILED DESCRIPTION

Figure 11:
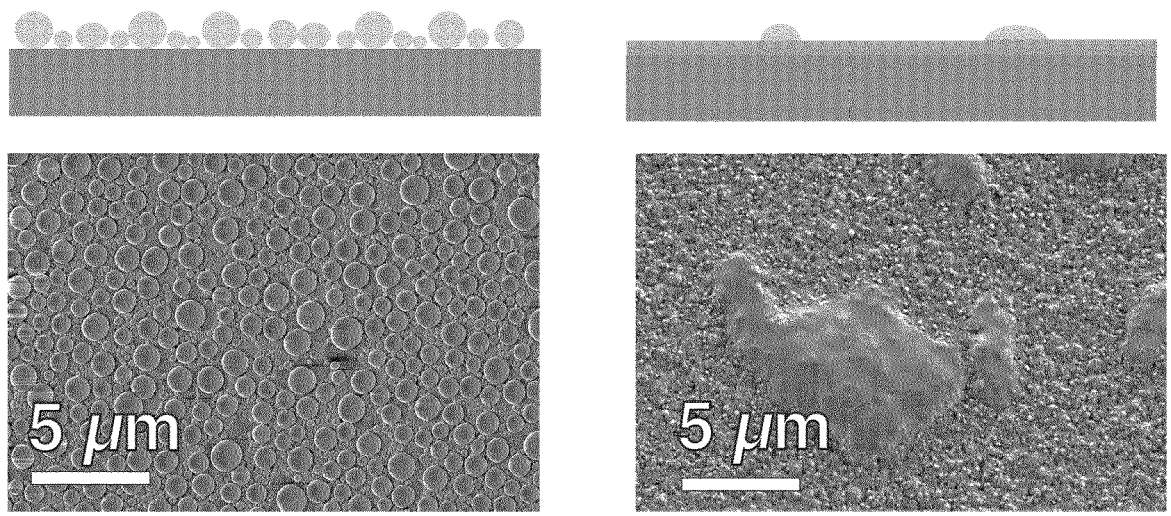
FIG. 11 shows scanning electron microscope (SEM) images of gallium deposited by thermal evaporation on a PDMS substrate and gallium deposited by thermal evaporation on a PDMS substrate previously coated with a layer of 60 nm of gold; scale bar is 5 μm.
Figure 12:
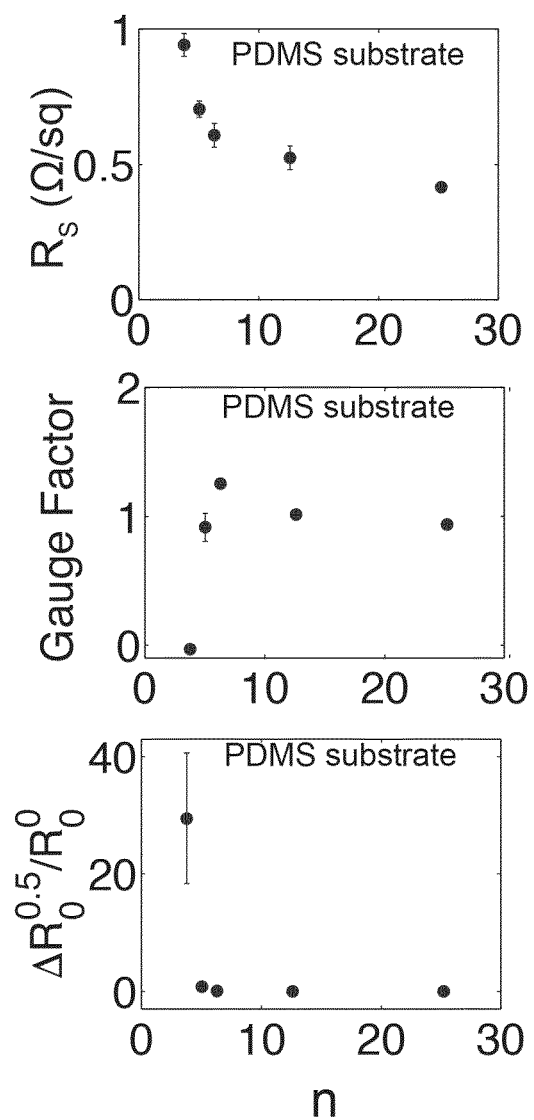
FIG. 12 shows sheet resistance, gauge factor and relative increase in resistance at rest after stretching to 50% as a function of the ratio n between the number of atoms of liquid metal and the number of atoms of solid metal in the resulting biphasic (solid-liquid) layer or film.

As depicted in FIG. 1, during a first method step, a substrate 30 is provided. The substrate 30 may be an elastomeric substrate, 20 for instance a PDMS substrate. The thickness of the substrate 30 may range from 1 μm to 1 mm according to the needs and/or circumstances. Still by way of non-limiting example, providing the substrate 30 may comprise spin coating a PDMS layer on a carrier 100 (not depicted), for instance a silicon carrier (wafer or the like), curing the layer 30 at 80° C. and removing the carrier.

During a second step, as depicted in FIG. 2, the substrate 30 is coated with a thin film 40 of a solid conductive metal; by way of example, the film 40 may be provided on the substrate 30 by sputtering gold (Au) on the substrate 30. Still by way of example, the final thickness of the gold film 40 may amount to 60 nm.

During a third step as depicted in FIG. 3, one or more liquid metals are deposited on the film 40 by thermal evaporation.

During the third step, the liquid metal (for instance gallium Ga) diffuses into the solid film 40 and alloys with the solid film to 5 form an alloy (for instance $AuGa_2$ in case Au is used for forming the solid conductive layer 40 and Ga is used as a liquid metal). Moreover, once the solid film is totally alloyed, the liquid metal starts to accumulate so that percolating paths and bulges of liquid metal are formed.

The situation at the end of the third step is therefore that depicted in FIGS. 3 and 4, namely with a conductive film or layer 43 comprising both a solid phase (the alloy) 41 and a liquid phase, namely the percolating paths and/or bulges 42 of liquid metal dispersed in the alloy 41.

For the sake of clarity, reference is made to FIGS. 5, 5a and 6 (with FIG. 5a showing an enlarged view of a portion of FIG. 5) showing schematic views of the film 43.

As apparent in particular from FIGS. 5 and 5a, the biphasic conductive film or layer 43, as anticipated above, comprises the 20 solid metallic alloy 41 (for instance $AuGa_2$) and the percolating paths and bulges 42 of liquid metal (for instance Ga).

The advantages of a biphasic conductive film of the kind disclosed above are schematically depicted in FIG. 6; it appears in fact clearly from FIG. 6, that when the film 43 is subjected to strain (for instance by subjecting to strain or stretch or the like the substrate 30), microcracks eventually formed in the solid phase 41 (the alloy) are filled by the liquid phase, so that the electrical conductivity of the layer or film 43 is maintained (electrical current flows across both the solid and liquid phases).

As to the liquid metals, gallium and a gallium-based alloy may be used according to the present invention; however, gallium has revealed to provide the best results since the stoichiometry of the evaporated film is the same as the stoichiometry of the original material. Moreover, as to the deposition of the liquid metal, thermal evaporation of one or both of the above mentioned gallium and gallium-based alloy has revealed to be the most preferred solution.

As to the solid metal(s) to be used for the formation of the 10 alloying layer 40, one of Au, Pd, Pt and Ir and an alloy thereof may be used according to the present invention.

Moreover, within the frame of the present invention several parameters of the thermal evaporation step (FIG. 3) have been investigated. For instance, the atomic ratio $n_{Ga}/n_{Au}$ (i.e. the ratio between the number of gallium atoms and the number of gold atoms in the film 43) offering the best results in terms of elevated conductivity and stretchability of the biphasic film 43 has been investigated. In this respect, a ratio $n_{Ga}/n_{Au} \geq 2$, more particularly corresponding to 13, has revealed to offer the best results.

The most convenient thickness for the alloying solid layer or film 40 has been investigated too; in this respect, for each of Au, Pt, Pd and Ir a thickness of about 60 nm ($\geq 10$ nm and $\leq 1000$ nm) offered the best electromechanical properties and/or results.

According to the present invention, during an optional further step (not depicted in the drawings), the biphasic film 43 may be patterned so as to obtain the desired conductive arrays and/or paths, films, lines or the like wherein for the purpose of patterning the film 43, for instance one or both of stencil and photolithography may be used. Still according to the present invention, and depending on the needs and/or circumstances, the biphasic film or array 43 can be encapsulated during a further step (not depicted in the drawings), for instance by spin-coating a further PDMS layer.

Still according to the present invention and depending on the needs and/or circumstances, during a further optional step not depicted in the drawings, one or more through vias can be formed in the upper encapsulation layer so as to expose one or more portions of the conductive biphasic film or array 43, wherein the exposed portions can be used for instance as contacting pads for electrical connection of the film 43, for instance wiring connection or stacking and connecting multiple metallized layers.

The above mentioned patterning and/or encapsulation and/or 15 wiring steps are not disclosed in detail for the sake of conciseness.

In the following, reference is made to FIGS. 7, 7a, 8, 8a, 9, 9a, 10 and 10a, wherein FIGS. 7a, 8a, 9a and 10a show enlarged view of portions of the biphasic film depicted in FIGS. 7, 8, 9 and 10, respectively. Moreover, in FIGS. 7, 7a, 8 and 8a the biphasic film showed therein is not subjected to any strain, whilst to the contrary, in FIGS. 9, 9a, 10 and 10a the biphasic film is subjected to a strain amounting to 50%.

Moreover, it has to be noted that, within the meaning of the following disclosure, a 50% applied strain has to be understood as meaning that a 50% strain was applied to the elastomeric substrate underlying the biphasic film, for instance the substrate depicted in FIG. 1.

The real SEM images of the drawings relate to a $AuGa_2$ biphasic 30 conductive film with a ratio $n_{Ga}/n_{Au}$ corresponding to 13 formed according to the present invention. Comparing the images 9, 9a, 10 and 10a with the images 7, 7a, 8 and 8a, respectively, confirms that, in the case of a biphasic conductive film according to the present invention, when the biphasic film is subjected to a strain, for instance when the film is stretched, the liquid metal (for instance gallium) is able to flow and fill in the cracks eventually induced by the stretch. In particular, no degradations of its electrical performance (essentially its conductivity) arise up to 80% mechanical strain.

It has therefore been demonstrated with the above description that biphasic films and manufacturing methods thereof according to the present invention allow to obtain the wished results, thus overcoming the drawbacks affecting the prior art conductive films (either solid or liquid) and manufacturing methods thereof.

It has in particular been demonstrated by means of the above disclosure that according to the present invention, both stretchable and non-stretchable conductive interconnections (in particular conductive micro interconnections) may be formed. By way of example, as described, stretchable interconnections may be formed by forming the biphasic film according to the present invention on a stretchable substrate, for instance a rubber substrate, in particular a PDMS substrate. However, non-stretchable interconnections may be formed as well, for instance by forming the biphasic film on a non-stretchable substrate.

Whilst the present invention has been clarified by means of the above description of its embodiments as depicted in the drawings, the present invention is not limited to the embodiments depicted in the drawings and/or described above.

The invention claimed is:

1. A method for manufacturing an electrical conductor, said method comprising:

depositing a solid metal layer on a substrate;

depositing a liquid metal on said solid metal layer;

allowing said liquid metal and said solid metal layer to form an alloy by diffusion of said liquid metal into said solid metal layer so as to form a solid conductive layer of said alloy;

allowing said liquid metal to further wet and infiltrate said alloy so as to form percolating paths of said liquid metal in said solid conductive layer, thus forming a biphasic conductive layer comprising said alloy as a solid phase and said percolating paths of said liquid metal as a liquid phase dispersed in the solid phase;

allowing said liquid metal to further accumulate into bulges, locally yet randomly, on or within said biphasic conductive layer; and controlling a ratio n between a total number of atoms of said liquid metal and a total number of atoms of said solid metal in said biphasic layer to be between 2 and 50.

2. The method according to claim 1, wherein said liquid metal is deposited on said solid metal layer by thermal vapour deposition of said liquid metal.

3. The method as claimed in claim 1, wherein said liquid metal comprises one of gallium or a gallium-based alloy.

4. The method as claimed in claim 1, wherein said solid metal layer is sputtered on said substrate.

5. The method as claimed claim 1, wherein said solid metal layer is made of one of Au, Pd, Pt, Ir, or an alloy thereof.

6. The method according to claim 1, wherein said solid metal layer has a thickness between 10 and 1000 nm.

7. The method as claimed in claim 1, wherein said substrate is an elastomeric substrate.

8. The method as claimed in claim 1, wherein said method further comprises patterning said biphasic conductive layer or film so as to form at least one biphasic strip.

9. The method as claimed in claim 8, wherein said biphasic conductive layer is patterned using one of stencil and photolithography.

10. The method as claimed in claim 1, wherein said method further comprises encapsulating said biphasic conductive layer by forming an encapsulation layer on said biphasic conductive layer.

11. The method as claimed in claim 10, said method further comprising forming at least one through via in said encapsulation layer so as to expose at least a portion of said biphasic conductive layer.

* * * * *